United States Patent
Friedrich et al.

(10) Patent No.: US 9,517,335 B2
(45) Date of Patent: Dec. 13, 2016

(54) IMPLANTABLE ELECTRICAL LINE

(71) Applicant: Biotronik SE & Co. KG, Berlin (DE)

(72) Inventors: Michael Friedrich, Kleinmachnow (DE); Gernot Kolberg, Berlin (DE); Timo Frenzel, Berlin (DE)

(73) Assignee: Biotronik SE & Co. KG, Berlin (DE)

( * ) Notice: Subject to any disclaimer, the term of this patent is extended or adjusted under 35 U.S.C. 154(b) by 0 days.

(21) Appl. No.: 14/804,154

(22) Filed: Jul. 20, 2015

(65) Prior Publication Data

US 2016/0045722 A1 Feb. 18, 2016

Related U.S. Application Data

(60) Provisional application No. 62/036,628, filed on Aug. 13, 2014.

(51) Int. Cl.

| | |
|---|---|
| *A61N 1/05* | (2006.01) |
| *A61N 1/08* | (2006.01) |
| *H01B 7/02* | (2006.01) |
| *H01B 7/06* | (2006.01) |
| *H01R 11/11* | (2006.01) |
| *H01B 3/47* | (2006.01) |
| *A61N 1/375* | (2006.01) |
| *A61N 1/39* | (2006.01) |
| *A61N 1/37* | (2006.01) |
| *A61N 1/362* | (2006.01) |
| *H01B 7/04* | (2006.01) |

(52) U.S. Cl.
CPC ............... *A61N 1/056* (2013.01); *A61N 1/05* (2013.01); *A61N 1/08* (2013.01); *A61N 1/375* (2013.01); *A61N 1/3718* (2013.01); *A61N 1/3968* (2013.01); *H01B 3/47* (2013.01); *H01R 11/11* (2013.01); *A61N 1/362* (2013.01); *A61N 2001/086* (2013.01); *H01B 7/048* (2013.01)

(58) Field of Classification Search
USPC .................................................. 607/116, 122
See application file for complete search history.

(56) References Cited

U.S. PATENT DOCUMENTS

| | | |
|---|---|---|
| 2004/0059404 A1 | 3/2004 | Bjorklund et al. |
| 2010/0174348 A1 | 7/2010 | Bulkes et al. |
| 2011/0218603 A1* | 9/2011 | Victorine ................. A61N 1/05 607/116 |

(Continued)

FOREIGN PATENT DOCUMENTS

| | | |
|---|---|---|
| WO | 2009137186 A1 | 11/2009 |
| WO | 2010078552 A1 | 7/2010 |
| WO | 2010126877 A1 | 11/2010 |

OTHER PUBLICATIONS

European Search Report received from EP Application Serial No. 15168078.2.1652 on Dec. 9, 2015, 7 pages.

*Primary Examiner* — Carl H Layno
*Assistant Examiner* — Jon Eric C Morales
(74) *Attorney, Agent, or Firm* — ARC IP Law, PC; Joseph J. Mayo (57) ABSTRACT

An implantable electrical line including a lead, wherein the lead includes at least one helically wound electrical conductor. The at least one helically wound electrical conductor is surrounded by a fiber braid, which is formed by at least two fibers or fiber bundles, and wherein the at least two fibers or fiber bundles are interwoven and wound around the electrical conductor in opposite winding directions.

12 Claims, 7 Drawing Sheets

(56) References Cited

U.S. PATENT DOCUMENTS

| | | | |
|---|---|---|---|
| 2012/0029335 A1* | 2/2012 | Sudam | A61N 1/05 600/374 |
| 2012/0109270 A1 | 5/2012 | Foster | |
| 2012/0158109 A1 | 6/2012 | Bartels et al. | |
| 2014/0350654 A1 | 11/2014 | Olsen et al. | |

* cited by examiner

IMPLANTABLE ELECTRICAL LINE

This application claims the benefit of U.S. Provisional Patent Application 62/036,628 filed on 13 Aug. 2014, the specification of which is hereby incorporated herein by reference.

BACKGROUND OF THE INVENTION

Field of the Invention

Embodiments of the invention generally relate to an implantable electrical line having an elongate electrical lead.

Description of the Related Art

Generally, implantable electrical lines are used for example as electrode lines (also referred to as "electrodes") for cardiac pacemakers or defibrillators and are used to transmit electrical pulses from a cardiac pacemaker or defibrillator to electrode poles at or in the vicinity of a distal end of the electrode line. Also, typically, the implantable electrical lines are used conversely to transmit electrical signals from one or more electrode poles to the cardiac pacemaker or defibrillator. To this end, an electrode line typically has one or more electrical conductors, which form one or more leads. Generally, in implantable electrical lines, such as electrode lines, a coil which is formed by one or more electrical conductors wound helically is preferably used as a lead since on the one hand it provides an inner lumen for a guide wire and on the other hand a wound wire is much more stable with respect to permanent bending stress.

Typically, a coil as a lead has one or more disadvantages, which need to be overcome.

For example, generally, implantable heart electrodes such as electrode lines for cardiac pacemakers or defibrillators are subjected to different mechanical stresses. In the case of implantation and explantation of electrode lines, typically, high tensile forces may occur. If the electrode line is arranged in an unfavorable position, generally, radial pressures can be produced, for example between the collarbone and the first rib. A conventional coil is generally not able to cope with such forces. In the case of tensile forces, typically, the coil composite contracts, and in the case of radial pressures the coil composite is disturbed and the coil is at risk of breaking The coil on the one hand, for example in embodiments of the invention as discussed herein below, may be soft and flexible to not provoke any reactions in the heart and on the other hand may be stable with respect to torsion such that the electrode line may be screwed in.

In addition, generally, elongate electrical lines have the disadvantage that a contained electrical conductor can heat up in an MRI scanner because the alternating magnetic fields prevailing in the MRI scanner induce electrical currents in the electrical conductor that are not insignificant. Therefore, typically, cardiac pacemaker patients cannot generally be examined in a magnetic resonance imaging (MRI) scanner or can only be examined in this way to a limited extent.

Specifically, at least one stimulation electrode line is typically connected to implantable cardiac pacemakers or defibrillators. Generally a stimulation electrode line at its proximal end is intended to be connected to a cardiac pacemaker or defibrillator and therefore has a standardized electrical terminal, and, at its distal end intended for placement in the heart, has one or more electrode poles. Such an electrode pole, generally, is used to deliver electrical pulses to the tissue (myocardium) of the heart or to sense electrical fields in order to sense cardiac activity, also known as sensing. For this purpose, electrode poles typically form electrically conductive surface portions of an electrode line. Electrode poles are typically provided as ring electrodes in the form of a ring around the electrode line or in the form of a point electrode or tip electrode at the distal end of the electrode line. The electrode poles are generally electrically conductively connected via one or more electrical conductors to contacts of the electrical terminal of the electrode line at the proximal end thereof. One or more electrical conductors, which typically electrically connect one or more of the electrode poles to one or more of the contacts, thus generally run between the contacts of the electrical terminal of the electrode lines at the proximal end thereof and the electrode poles at the distal end of the electrode line. These electrical conductors, generally, can be used on the one hand for transmission of stimulation pulses to the electrode poles and on the other hand for transmission of electrical signals, received by means of the electrode poles, to the proximal end of the electrode line, also referred to herein as a function line. Such function lines are generally electrical conductors necessary for the functions of the respective electrode line and as such are exposed to the risk that electrical currents will be induced therein as a result of external alternating magnetic fields. Typically, the currents for example may lead to an undesirable heating of the function lines or of the electrode poles connected thereto or may lead to the delivery of corresponding currents via the electrode poles to surrounding tissue and therefore to a heating of the surrounding tissue.

In order to make an electrode line less sensitive for MRI energies, generally, it is expedient to equip the coil with a high inductance. This is typically achieved with as many windings as possible, which would in turn make the coil mechanically unstable.

Generally, the mechanical disadvantages of a coil are compensated for by external protection in the case of known electrode lines. Outer tubes that are as stable as possible are typically used for electrical insulation and for mechanical protection. Generally, braided tubes are often used in the catheter field in order to make the catheter stable with respect to kinks and torsion. In the electrode field, typically, such concepts have not been previously used. Electrodes of which the coils have been replaced by cables, generally, do not have a lumen for the guide wire and are implanted using special catheters.

Otherwise, typically, the coil geometries would have to be held in the geometric dimensions that are stable when in use.

For example, a disadvantage of typical coils as leads is wherein a coil that has to be mechanically protected by its insulation generally limits the design possibilities of a product.

Another disadvantage of typical coils as leads is wherein a coil that includes conflicting mechanical or electrical properties is typically always a compromise in both directions, which leads to properties of the product in need of improvement. For example, as another disadvantage, a braided tube, of which the insulation is increased, is generally relatively stiff and cannot improve the torsion properties of the coil itself Generally, additional components in a typical electrode that are intended to improve the magnetic resonance (MR) properties always have mechanical disadvantages. Therefore, a typical electrode including such additional components may thus be more rigid or thicker. In addition the fatigue strength of the electrode may then be impaired in particular when electrically effective components are integrated in the therapeutic circuit in series connection.

In order to make an electrode insensitive with respect to the high-frequency energies from magnetic resonance tomography (MRT), there is a need for additional components, such as inductive filters, band-stop filters or additional energy diverters.

BRIEF SUMMARY OF THE INVENTION

At least one embodiment of the invention provides an implantable electrical line with as few disadvantages as possible compared with typical electrode lines.

One or more embodiments of the invention include an implantable electrical line, which includes a lead, wherein the lead may include at least one helically wound electrical conductor. In at least one embodiment, the at least one helically wound electrical conductor may be surrounded by a fiber braid, which is formed by, or includes, at least two fibers or fiber bundles that are interwoven and wind around the at least one helically wound electrical conductor in opposite winding directions.

In one or more embodiments, the implantable electrical line includes a new type of lead structure, which overcomes many disadvantages of the typical coil.

Embodiments of the invention may combine a coil directly with a braid. In at least one embodiment, the coil and braid may form a mechanical unit or mechanical structure. One or more embodiments of the invention includes an electrical lead of an implantable electrical line, wherein the electrical lead may be formed by, or may include, at least one wire and at least two fibers or fiber bundles. In at least one embodiment, one or more wires may be wound into a coil and at least two fibers or fiber bundles may be braided around the coil and may be mechanically connected to the coil at least at one end.

In one or more embodiments, the electrical line may include one or more of the following properties:
Tensile stability, torsional rigidity, radial pressure stability, kink stability, reduction of the high frequency (HF) transmission properties and reduction of the electrical resistance.

In at least one embodiment, flexibility and long-term stability of the lead is largely maintained. Due to the structure of the lead, according to one or more embodiments of the invention, new coil geometries may be implemented, unlike previous typical leads that were too unstable such as thin coil wires, single coils, coils with high inductance, etc.

At least one embodiment of the invention includes one or more leads that include an inner lumen and may be produced with or include the implantable electrical line. In one or more embodiments, the leads may include high flexibility and high fatigue strength and simultaneously may overcome at least some of the following disadvantages, at least in part:
deficient tensile strength,
poor radial pressure stability,
poor torsion transmission, and
poor high frequency (HF) damping.

At least one embodiment of the invention overcomes one or more disadvantage of typical coils as leads.

By way of one or more embodiments, the at least one helically wound electrical conductor may form, or may include, a coil that is electrically conductively and mechanically connected at one or at both longitudinal ends to an electrically conductive sleeve. In at least one embodiment, the fibers may be mechanically connected to the electrically conductive sleeve and/or the electrically conductive sleeves.

In one or more embodiments, at least one of the sleeves of the electrically conductive sleeves may form, or may include, a capacitor with a coil sleeve which is concentric with the electrically conductive sleeve(s), discussed above, and which is electrically insulated from the electrically conductive sleeve(s) by a dielectric.

By way of one or more embodiments, the at least one helically wound electrical conductor may be formed by, or may include, a wire made of one or more of the following metals: Pt, Pt/Ir, MP35N, elgiloy, high-grade steel, copper, molybdenum, tantalum, gold, zirconium, iron-containing alloys, tantalum/tungsten alloys, refractory metals such as niobium or titanium, silver, palladium, conductive polymers or polycondensates and combinations thereof in a sheath-core wire.

In at least one embodiment, the fibers may be formed from, or may include, one or more of the following metals or plastics: Pt, Pt/Ir, MP35N, elgiloy, high-grade steel, copper, molybdenum, tantalum, gold, zirconium, iron-containing alloys, tantalum/tungsten alloys, refractory metals such as niobium or titanium, silver, palladium, conductive polymers or polycondensates, and combinations thereof in a sheath-core wire, and polyetheretherketon (PEEK), polyamide, polyurethane, carbon fibers, polyethylene, polyimide, aramid, polytetafluoroehtylene (PTFE), ethyleneteta-fluoroethylene (ETFE), spider silk fabrics, spider silk fibers, and artificial spider silk.

In one or more embodiments, the at least one helically wound electrical conductor may be insulated by a coating.

In at least one embodiment, the fibers may be insulated by a coating.

In one or more embodiments, an insulation, for example an insulating tube, may be arranged between the at least one helically wound electrical conductor and the fibers.

In at least one embodiment, the fiber braid formed by the fibers may include both electrically non-conductive fibers made of plastic and electrically conductive fibers made of metal.

In one or more embodiments, the implantable electrical line may include a lead, which may be formed as or include one or a single portion or in a number of or multiple portions.

In at least one embodiment, the implantable electrical line may be or include a cardiac pacemaker and/or defibrillator electrode line and includes one or more electrode poles electrically connected to the lead.

In one or more embodiments, the lead may be formed such that the at least one helically wound electrical conductor and/or the fiber braid form or include inductors and/or capacitors, either alone or in combination with one another. In at least one embodiment, one or more of the inductors and capacitors may include filtering properties and/or may form or include a filter that damps at frequencies of the electromagnetic fields prevailing in magnetic resonance imaging (MRI) scanners. As such, in one or more embodiments, electrode lines that include a lead as discussed herein not only include advantageous mechanical properties, but may also be used in an MRI scanner.

At least one embodiment of the invention may include one or more of the following:
The electrical conductor forming the coil may be a flat wire.
The fibers of the fiber braid may include a diameter between 0.005 and 0.2 mm.
An insulating tube or an insulating additional braid may be located between the fibers of the fiber braid and the coil.
The fibers of the fiber braid may be electrically connected at both ends to the coil.

The fibers of the fiber braid may be connected only at one end to the coil.

The fibers of the fiber braid may be electrically completely insulated from the coil.

The fibers of the fiber braid may be capacitively connected at both ends to the at least one helically wound electrical conductor.

The fibers of the fiber braid may be capacitively connected at one end to the at least one helically wound electrical conductor and may be galvanically connected at the other end.

The fibers of the fiber braid may be capacitively connected at one end to the at least one helically wound electrical conductor and may be connected at the other end in an electrically open (high-resistive) manner.

The fibers of the fiber braid may be one or more of braided on a tube, surrounded by a coil and mechanically connected thereto at both ends.

The lead of an electrode may include a number of segments, wherein the segments may be connected in series.

A series connection of a number of lead segments, wherein the winding direction of the coil of the respective lead segment may change from one lead segment to the other, such that a damping behavior is influenced.

The coil may be surrounded by a double-layer or a multi-layer fiber braid.

Both the at least one helically wound electrical conductor and the fibers of the fiber braid may include a coating made of PEEK, polyamide, polyurethane, carbon fibers, polyethylene, polyimide, aramid, PTFE and/or ETFE.

A series connection between one or more leads and/or one or more coils.

BRIEF DESCRIPTION OF THE DRAWINGS

The above and other aspects, features and advantages of at least one embodiment of the invention will be more apparent from the following more particular description thereof, presented in conjunction with the following drawings, wherein.

DETAILED DESCRIPTION OF THE INVENTION

The following description is of the best mode presently contemplated for carrying out at least one embodiment of the invention. This description is not to be taken in a limiting sense, but is made merely for the purpose of describing the general principles of the invention. The scope of the invention should be determined with reference to the claims.

Figure 1:
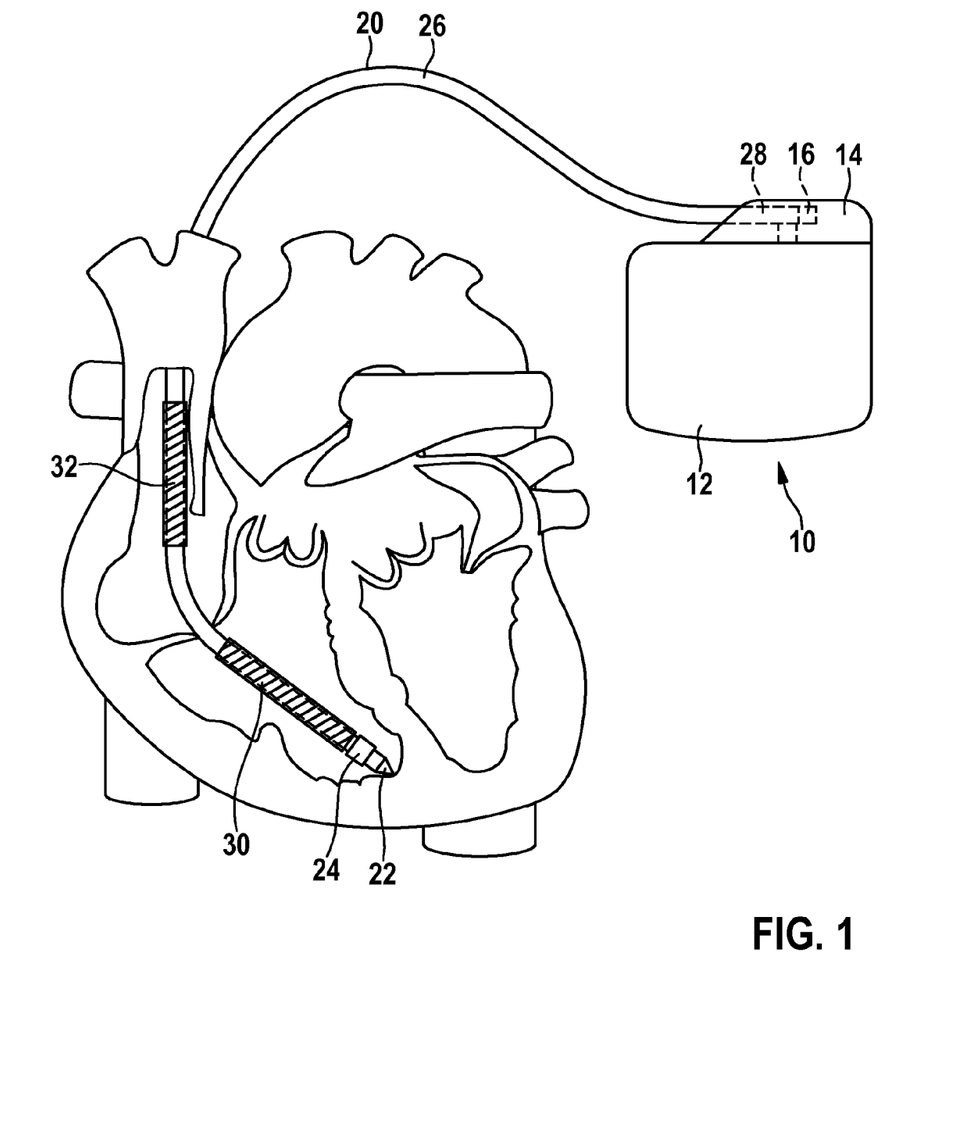
FIG. 1 shows an implantable heart stimulator and an implantable electrode line connected thereto.

FIG. 1 shows an implantable heart stimulator 10 and an implantable electrode line 20 connected thereto, according to one or more embodiments of the invention. In at least one embodiment, the implantable heart stimulator 10 may be a cardiac pacemaker or an implantable cardioverter/defibrillator (ICD). In at least one embodiment, the heart stimulator 10 may be a ventricular cardiac pacemaker and defibrillator. In one or more embodiments, the heart stimulator 10 may include one or more of dual-chamber cardiac pacemakers to stimulate the right atrium and the right ventricle, and biventricular cardiac pacemakers to stimulate the left ventricle and the right ventricle.

By way of at least one embodiment, the heart stimulator 10 may include a housing 12, wherein the housing 12 may include metal that is electrically conductive and may serve as a large-area electrode pole. One or more embodiments may include a terminal housing 14 fastened to the outer face of the housing 12, also referred to herein as a header. In at least one embodiment, the header may include contact sockets to receive plug contacts. In one or more embodiments, the contact sockets may include electrical contacts 16, wherein the electrical contacts 16 may be connected via corresponding conductors to an electronics unit or device arranged in the housing 12 of the heart stimulator 10.

In one or more embodiments, the electrode line 20 may be an implantable electrical line. At least one embodiment of the invention may include electrode poles in the form of a point or tip electrode 22, and a ring electrode 24 arranged in the vicinity thereof, at the distal end of the electrode line 20. In one or more embodiments, the electrode poles 22 and 24 may be used, depending on the function of a heart stimulator to which the electrode line 20 is connected, to sense electrical potentials of the heart tissue (myocardium), and/or to deliver electrical signals, for example to deliver stimulation pulses to the surrounding heart tissue. As shown in FIG. 1, in at least one embodiment, the electrode poles, such as the tip electrode 22 and the ring electrode 24, during use of the electrode line 20, may be located in the apex of the right ventricle of a heart.

By way of one or more embodiments, the tip electrode 22 and the ring electrode 24 may be electrically connected in each case via at least one electrical conductor 26.1 and 26.2 to a plug contact 28 at the proximal end of the electrode line 20. In at least one embodiment, the plug contact 28 may include electrical contacts that correspond to the electrical contacts 16 of the contact socket in the terminal housing 14 of the implantable heart stimulator 10. In one or more embodiments, the electrical conductors 26.1 and 26.2 in the electrode line 20 may be wound to form a common helix and form a lead 26 in the form of a co-radial coil lead. In at least one embodiment, the co-radial coil lead may include a co-radial wire coil, which is formed by two wires each wound to form a helix with identical diameter and pitch. Instead of a co-radial coil lead, one or more embodiments may include a number of coils coaxial to one another, wherein each coil of the number of coils coaxial to one another may include a different diameter. As such, one or more embodiments may include a coaxial coil lead. In at least one embodiment, the conductors 26.1 and 26.2 may transmit signals, referred to herein as function conductors. One or more embodiments may include a respective lead with one or more conductors, for example wires, which support the structure of the lead.

In at least one embodiment, the lead 26 may be formed by the electrical conductors 26.1 and 26.2, which connect the electrode poles 22 and 24 respectively to the electrical contacts of the plug 28 of the electrode line 20. In one or more embodiments, the lead 26 may be surrounded over the majority of its length by an insulating sleeve, such that electrical contact of the tissue of the heart is produced selectively via the electrode poles.

In at least one embodiment, the electrode poles 22 and 24 may be used to stimulate the heart tissues, such as by ventricular stimulation. In one or more embodiments, the electrode line 20 may include two electrode poles 30 and 32, which may include a greater area, may be used as defibrillation electrodes and may be formed by at least one bare helically wound wire.

It should be noted that the embodiments of the invention are explained herein on the basis of a right-ventricular pacemaker and defibrillator. However, at least one embodiment of the invention may include an ablation electrode line for example as a medical device, wherein the ablation electrode line, during use, may protrude into the heart of a patient, may be controlled by a device arranged outside the patient and may be connected to the device.

Figures 2, 3:
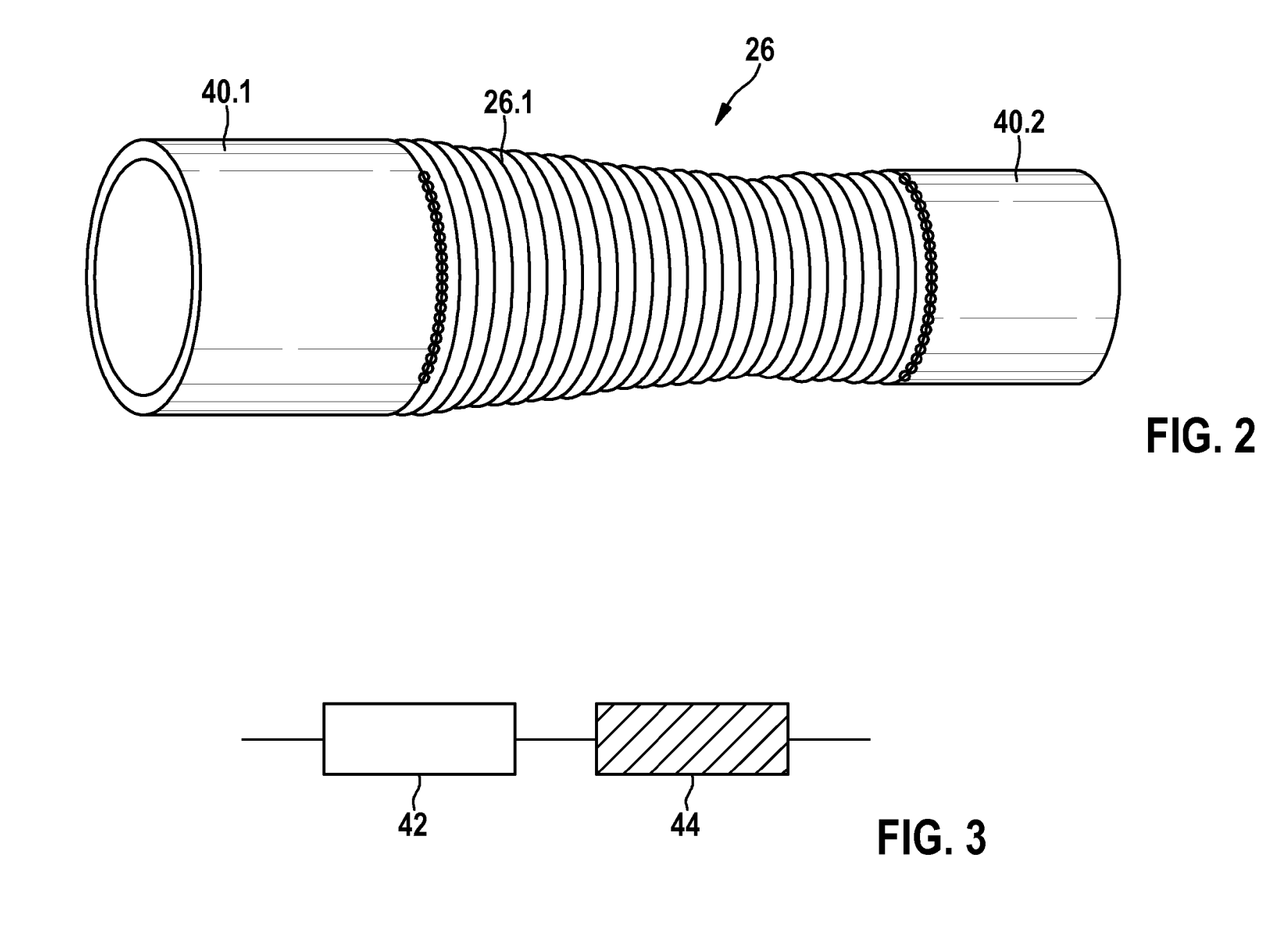
FIG. 2 shows a coil, wherein the ends thereof are welded to sleeves.
FIG. 3 shows an equivalent electrical circuit diagram for the coil of FIG. 2.

FIG. 2 shows a coil 26 of a lead, formed by a helically wound wire 26.1. In at least one embodiment, the longitudinal ends of the coil may be welded to sleeves 40.1 and 40.2. In one or more embodiment, such coils may be used for example as inner conductors in coaxially structured electrode lines. In at least one embodiment, the torsion to operate the screw mechanism may be transmitted via the coils. The equivalent electrical circuit diagram for the coil from FIG. 2 may be a series connection formed of resistor 42 and inductor 44; as shown in FIG. 3 according to one or more embodiments of the invention.

Figure 4:
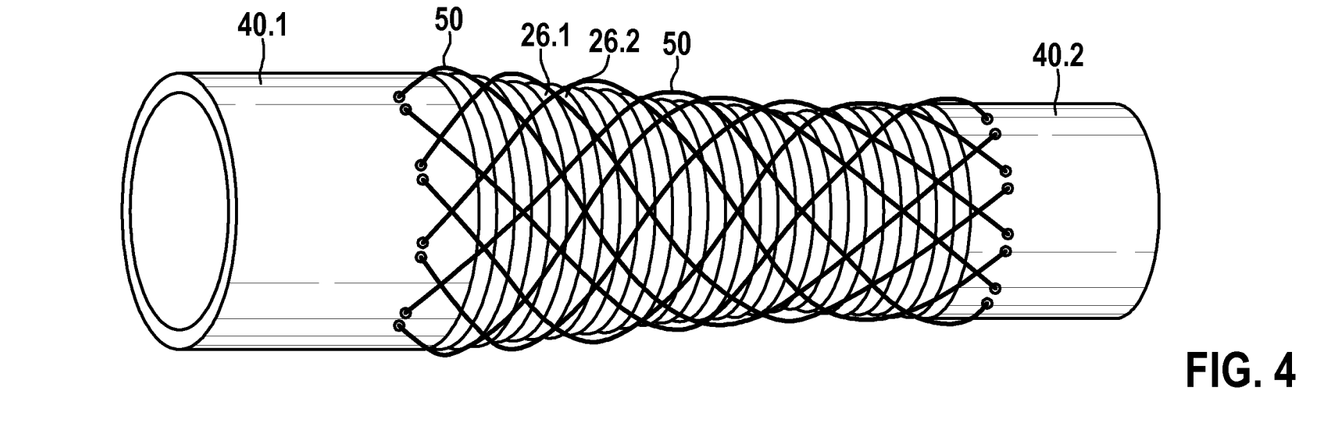
FIG. 4 shows a coil similar to the coil of FIG. 2 with a plurality of thin individual wires braided around the coil.

FIG. 4 shows a coil 26 similar to the coil of FIG. 2 with a plurality of thin individual wires 50 braided around the coil 26, thus forming a lead, according to one or more embodiments of the invention, with helically wound electrical conductor 26.1. In at least one embodiment, the helically wound electrical conductor 26.1 may form the coil 26, and may include a fiber braid formed from fibers 50 surrounding the coil. In one or more embodiments, the lead may be mechanically stable and suitable as an inner conductor in various electrode line constructions. In at least one embodiment, the lead may transmit torques in order to unscrew a fixation. In one or more embodiments, the lead may reliably transmit tensile forces such that the electrode line, of which the lead is part of, may be explanted.

In at least one embodiment, each of the individual wires 50 may include metal and may be a conductor or part of a conductor. Alternatively or in addition to individual wires that include metal, one or more embodiments may include fibers or filaments that include other materials, such as plastic. By way of one or more embodiments, individual wires that include metal may be referred to herein as "fibers".

In at least one embodiment, suitable materials for the metal wire 26.1 that forms the coil of the lead may include one or more of Pt, Pt/Ir, MP35N, elgiloy, high-grade steel, copper, molybdenum, tantalum, gold, zirconium, tantalum/tungsten alloys, refractory metals such as niobium and/or titanium, palladium, conductive polymers, polycondensates, and combinations thereof in a sheath-core wire, and iron-containing alloys, silver and combinations thereof in a sheath-core wire.

In one or more embodiments, suitable materials for the fibers 50 of the fiber braid may include metals, such as the metals of the coil of the lead as discussed above, and may include plastics, such as PEEK, polyamide, polyurethane, carbon fibers, polyethylene, polyimide, aramid, PTFE, ETFE, etc.

In at least one embodiment, a respective metal wire 26.1 that forms the coil may include a wire diameter between 0.03 and 0.2 mm. In one or more embodiments, if the coil 26 is a co-radial coil and is formed accordingly by a number of metal wires 26.1, the wires that form the coil may include different metals and/or may include the same material as the other wires forming the co-radial coil.

In at least one embodiment, the respective metal wire 26.1 of the coil 26 may be a flat wire.

In one or more embodiments, the fibers 50 of the fiber braid may include a diameter between 0.005 and 0.2 mm.

Figure 5:
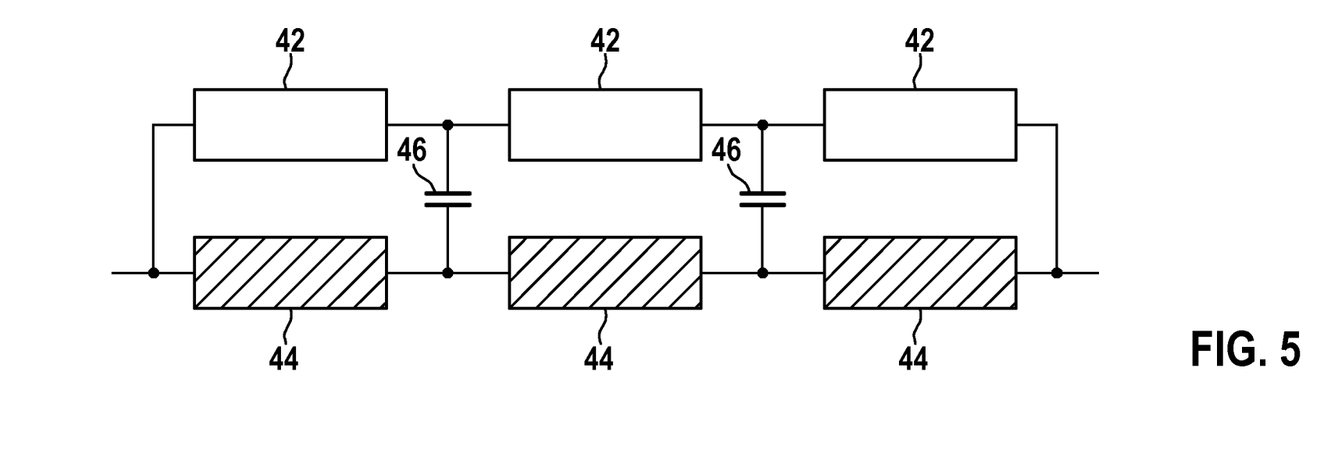
FIG. 5 shows an equivalent electrical circuit diagram for the coil of FIG. 4.

If the fibers 50 are formed by electrically conductive wires, at least one embodiment may include a capacitive coupling wherein the conductors formed by the individual wires 50 may be arranged very closely at the points of intersection with the coil. One or more embodiments may include an equivalent electrical circuit diagram as shown in FIG. 5 and may include capacitors 46, alternatively or in addition to ohmic resistors 42 and inductors 44.

Figure 6:
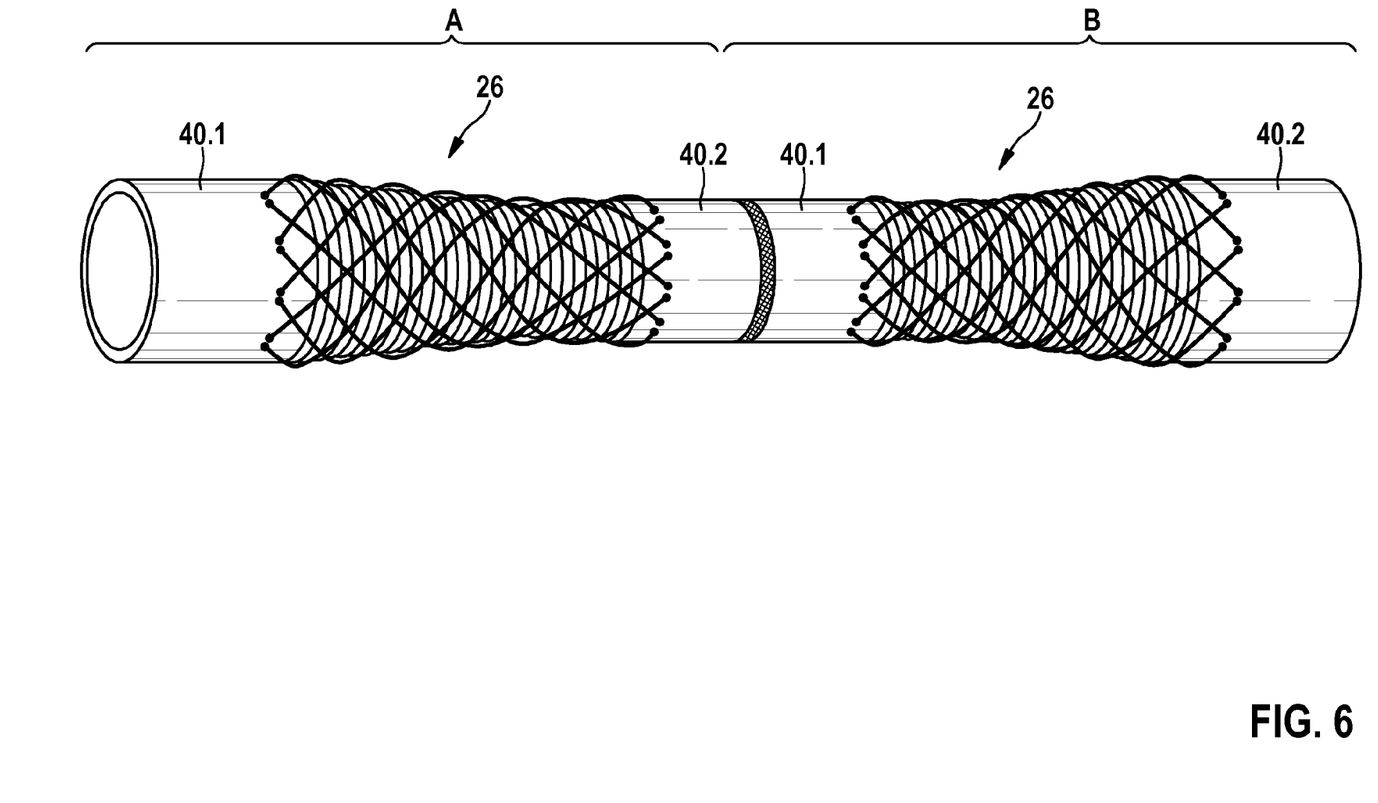
FIG. 6 shows a lead formed by two short lead segments connected in series.

FIG. 6 shows two short lead segments A and B according to one or more embodiments of the invention, which may be constructed in the manner of the lead construction shown in FIG. 3 and may be connected in series, wherein the winding direction of the two coils of the lead segments connected in series is opposite.

Figure 7:
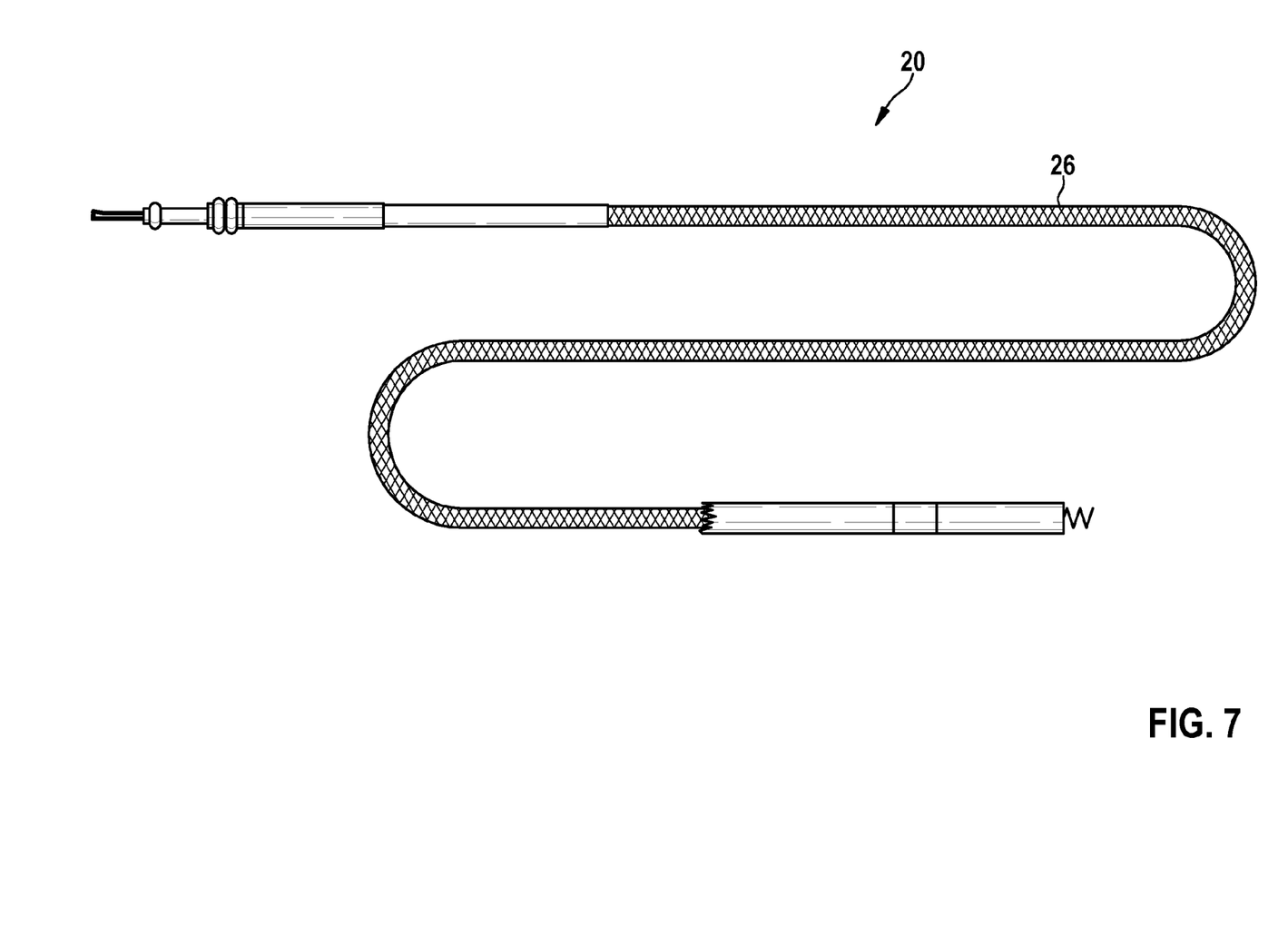
FIG. 7 shows an electrode line of which the outer conductor is formed by a braided outer coil.

FIG. 7 shows an electrode line 20, of which the outer conductor is formed by a braided outer coil 26, according to one or more embodiments of the invention. In at least one embodiment, the electrode line 20 may be resistant with respect to subclavian crush. In one or more embodiments, the electrode line 20 may include a respective inner conductor that may be braided. As such, in at least one embodiment, a torque may be transmitted particularly well between the head and the fixing helix, which may be unscrewed.

Figure 8:
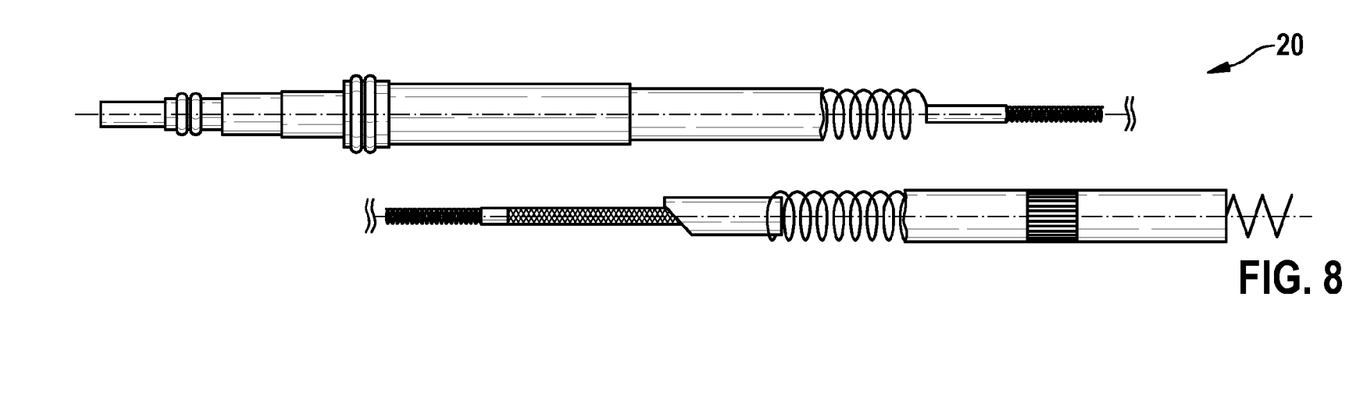
FIG. 8 shows an electrode line of which the inner conductor is formed by a combination of a first coil as a lead and a second lead according to one or more embodiments of the invention.

FIG. 8 shows an electrode line 20, of which the inner conductor is formed from a combination of a first coil as a lead and a second lead according to one or more embodiments of the invention. In at least one embodiment, the coil may include four individual filaments arranged in parallel as wound conductors 26.1, 26.2, 26.3 and 26.4 made of wire, which enable a low overall resistance of the lead. In the distal region of the lead, one or more embodiments may include a short braided lead segment, as shown in FIG. 9.

Figure 9:
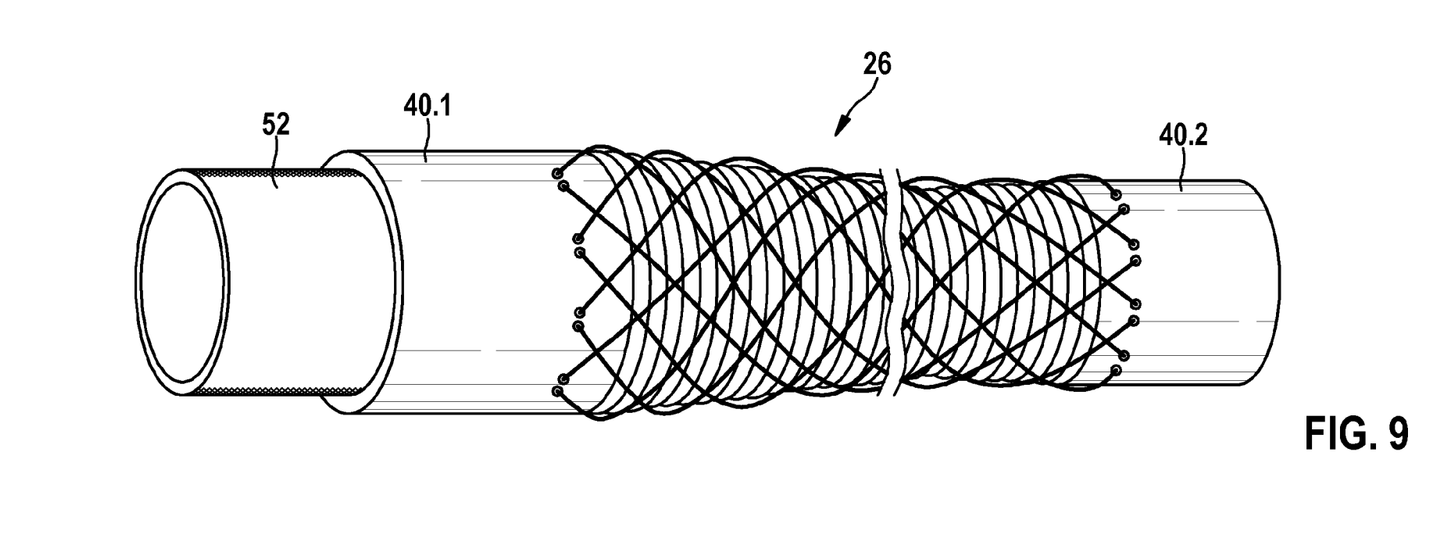
FIG. 9 shows a distal inner conductor segment, which is formed by a braided coil, of which the braid is welded on the left-hand side to a sleeve that was previously hammered onto the coil sleeve coated in an insulating manner.

FIG. 9 shows a distal inner conductor segment, according to one or more embodiments of the invention. In at least one embodiment, the distal inner conductor segment may be formed by a braided coil of which the braid is welded on the left-hand side to a sleeve 40.1, which was previously hammered onto a coil sleeve 52 coated in an insulating manner. As such, in one or more embodiments, an electrical capacitance may be produced between the inner coil sleeve 52 and the outer sleeve 40.1, which may form a capacitor. In at least one embodiment, the coil wire forming the conductor 26.1 may be coated in an electrically insulating manner. In one or more embodiments, the braid formed by the fibers 50 may be capacitively separated from the coil 26 at one end. In at least one embodiment, at the opposite end, the braid formed by the fibers 50 may be connected to the coil 26. In one or more embodiments, the coil used in the lead segment may include two parallel coil filaments, which may be thinner than the coil wire 26.1 of the lead coil 26 as shown in FIG. 8. As such, by way of at least one embodiment, the inductance of the lead segment may be considerably increased compared with a typical coil. In one or more embodiments, the capacitive properties of the dielectrically coated coil sleeve 52 and the inductive properties of the coil components may be matched to one another such that an equivalent circuit diagram as shown in FIG. 10 is produced.

Figure 10:
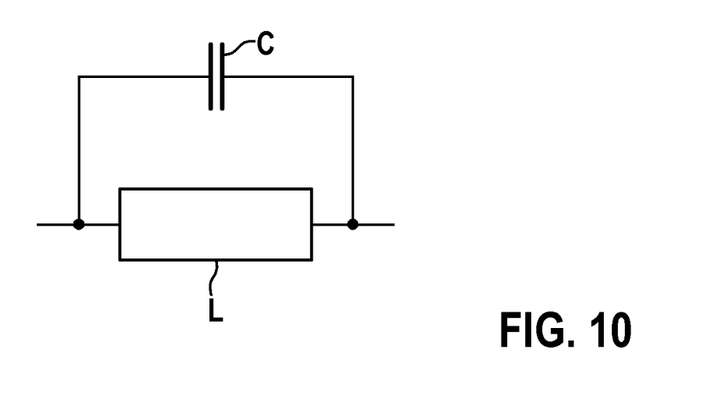
FIG. 10 shows the equivalent electrical circuit diagram for the construction of FIG. 9.

FIG. 10 shows the resultant electrical circuit diagram of the lead construction of FIG. 9, according to one or more embodiments. In at least one embodiment, the coil segment may form an inductor L, with a capacitor C being connected parallel thereto, wherein the characteristic of the lead construction corresponds to that of a band-stop filter. In at least one embodiment, the capacitance of C may be adapted or selected such that the resonance of the filter enables a good HF-damping effect close to excitation frequencies of the HF antenna of the MRI scanner. In one or more embodiments, with a 1.5 T MRI scanner, the excitation frequencies of the HF antenna may be approximately 64 MHz in an actual filter, wherein both components, the coil and the fiber braid, may include inductive, capacitive and resistive portions.

With a series connection of a number of such elements, according to at least one embodiment, all elements may include the same resonance frequency in order to intensify the overall filter effect, or individual elements may be adapted or selected with other frequencies, such as frequencies of a 3 T MRI scanner, with approximately 128 MHz.

One or more embodiments of the invention may include a suitable capacitor of various types.

(a) For example, as shown in FIG. 9, one or more embodiments may include a previously applied dielectric layer between two concentric sleeves at one end of a lead or of a lead segment. In at least one embodiment, the dielectric layers may be formed by or include materials including one or more of silicon carbide, alumina, oxidized surfaces of the sleeves, parylene, polyimide, and polyethylene.

(b) For example, as shown in FIG. 9, at least one embodiment may include a capacitor in both end sleeves formed by two concentric sleeves insulated from one another.

(c) For example, alternatively or additionally to capacitors formed by sleeves, one or more embodiments may include a capacitor formed between the braid fiber/fiber bundles. In at least one embodiment, only half of the braid fibers/fiber bundles may be contacted to one end sleeve galvanically, and at the other end sleeve mechanically, but not galvanically. In one or more embodiments, the other half of the braid fibers/fiber bundles, which may be separated from the others, for example by a dielectric coating, may be contacted accordingly at the opposite end.

(d) For example, alternatively or additionally, one or more embodiments may include a capacitor formed between the insulated braid fiber/fiber bundles, which are only contacted galvanically to an end sleeve, and an electrically conductive layer, such as a metal layer contacted to the other end sleeve, applied externally to the fiber braid insulation.

Figure 11:
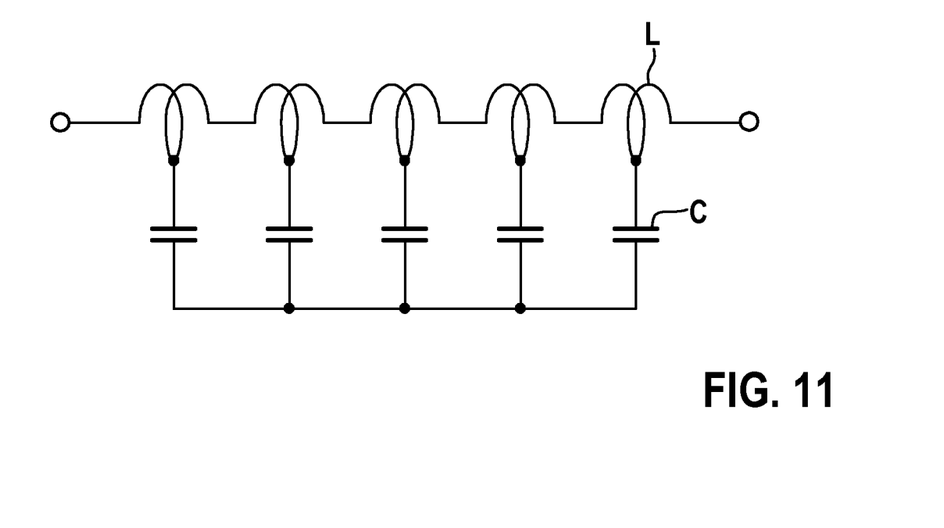
FIG. 11 shows an equivalent electrical circuit diagram of a further variant of the lead according to one or more embodiments the invention.

(e) For example, alternatively or additionally, in one or more embodiments, the braid fibers 50 or corresponding fiber bundles may not be galvanically contacted to one or both of the end sleeves, but may serve to capacitively couple the individual windings along the coil. As such, in at least one embodiment, the braid formed of the fibers 50 may be contacted either in an electrically floating manner or only at one end to the coil 26. In one or more embodiments, the distributed capacitance produced therefrom may lead to the desired filter resonance. The electrical circuit diagram as shown in FIG. 11 may be summarized as equivalent, discrete components L and C as shown in FIG. 10, according to one or more embodiments of the invention.

By way of at least one embodiment, the concentric sleeves of the capacitor variant (a) may be combined as follows:

(1) For example, as shown in FIG. 9, at least one embodiment may include either an inner or an outer sleeve that is first dielectrically coated beforehand, then the sleeves may be slid one inside the other and hammered together.

(2) For example, as (1), however, in one or more embodiments, the sleeves may be joined together by different thermal expansion. For example, in at least one embodiment, the inner sleeve may be cooled, and the outer sleeve may be heated, wherein the sleeves may be slid one inside the other and may then form a fixed connection, such as a press fit, after temperature adjustment.

(3) For example, in at least one embodiment, the sleeves may be uncoated beforehand. In one or more embodiments, the sleeves may be slid one inside the other, for example as a looser fit, and immersed in an electrolyte solution, then current may be passed from one sleeve to the other. As such, in at least one embodiment, a layer may be formed between the sleeves using galvanic oxidation. In one or more embodiment, the layer may then serve as a dielectric. By way of one or more embodiments, suitable materials for at least one of these sleeves may include materials that may anodize, such as one or more of titanium, tantalum, niobium and aluminum.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

LIST OF REFERENCE SIGNS

10 implantable heart stimulator
12 housing
14 terminal housing
16 contacts
20 electrode line
22 tip electrode
24 ring electrode
26.1, 26.2 electrical conductor
26 (coil) lead
28 plug contact
30, 32 electrode pole
40.1, 40.2 sleeve
42 ohmic resistor
44 inductor
46 capacitor
50 (wire) fiber
52 coil sleeve

What is claimed is:

1. An implantable electrical line comprising:
a lead or a lead segment, wherein said lead or said lead segment comprises at least one helically wound electrical conductor,
wherein the at least one helically wound electrical conductor is surrounded by a fiber braid comprising at least two fibers or fiber bundles,
wherein the at least two fibers or fiber bundles are interwoven and are wound around the at least one helically wound electrical conductor in opposite winding directions,
wherein the at least one helically wound electrical conductor and the fiber braid form one or more a inductors and capacitors, and
wherein the one or more of inductors and capacitors forms a filter that blocks at frequencies of electromagnetic fields prevailing in magnetic resonance imaging (MRI) scanners.

2. The implantable electrical line as claimed in claim 1, wherein the at least one helically wound electrical conductor forms a coil comprising two longitudinal ends, wherein the coil is electrically conductively and mechanically connected at one end of the two longitudinal ends end to an electrically conductive sleeve or at each end of the two longitudinal ends to an electrically conductive sleeve, and wherein the at least two fibers or fiber bundles are connected to one or more of the electrically conductive sleeve at the one end and the electrically conductive sleeves at the each end of the two longitudinal ends.

3. The implantable electrical line as claimed in claim 2, wherein at least one of the electrically conductive sleeves forms a capacitor with a coil sleeve, wherein the coil sleeve is concentric with the at least one electrically conductive sleeve and wherein the coil sleeve is electrically insulated from the electrically conductive sleeve or the electrically conductive sleeves by a dielectric.

4. The implantable electrical line as claimed in claim 1, wherein the at least one helically wound electrical conductor comprises a wire comprising one or more of Pt, Pt/Ir, MP35N, elgiloy, high-grade steel, copper, molybdenum, tantalum, gold, zirconium, iron-containing alloys, tantalum/tungsten alloys, refractory metals comprising niobium or titanium, silver, palladium, conductive polymers, polycondensates and combinations thereof in a sheath-core wire.

5. The implantable electrical line as claimed in claim 1, wherein the at least two fibers or fiber bundles comprise one or more metals or plastics comprising one or more of Pt, Pt/Ir, MP35N, elgiloy, high-grade steel, copper, molybdenum, tantalum, copper, gold, zirconium, iron-containing alloys, silver, combinations thereof in a sheath-core wire, polyetheretherketon (PEEK), polyamide, polyurethane, carbon fibers, polyethylene, polyimide, aramid, polytetafluoroethylene (PTFE), ethylenetetafluoroethylene (ETFE), spider silk fabrics, spider silk fibers, and artificial spider silk.

6. The implantable electrical line as claimed in claim 1, wherein the at least one helically wound electrical conductor is insulated by a coating.

7. The implantable electrical line as claimed in claim 1, wherein the at least two fibers or fiber bundles are insulated by a coating.

8. The implantable electrical line as claimed in claim 1, further comprising insulation between the at least one helically wound electrical conductor and the at least two fibers or fiber bundles.

9. The implantable electrical line as claimed in claim 1, wherein the fiber braid comprises electrically non-conductive fibers comprising plastic, and further comprises electrically conductive fibers comprising metal.

10. The implantable electrical line as claimed in claim 1, wherein the lead or the lead segment further comprises a single portion.

11. The implantable electrical line as claimed in claim 1, wherein the implantable electrical line is one or more of a cardiac pacemaker and a defibrillator electrode line, and further comprises one or more electrode poles electrically connected to the lead or the lead segment.

12. An implantable electrical line comprising:
a lead or a lead segment, wherein said lead or said lead segment comprises at least one helically wound electrical conductor,
wherein the at least one helically wound electrical conductor is surrounded by a fiber braid comprising at least two fibers or fiber bundles, and
wherein the at least two fibers or fiber bundles are interwoven and are wound around the at least one helically wound electrical conductor in opposite winding directions,
wherein the at least one helically wound electrical conductor forms a coil comprising two longitudinal ends,
wherein the coil is electrically conductively and mechanically connected at one end of the two longitudinal ends end to an electrically conductive sleeve or at each end of the two longitudinal ends to an electrically conductive sleeve,
wherein the at least two fibers or fiber bundles are connected to one or more of the electrically conductive sleeve at the one end and the electrically conductive sleeves at the each end of the two longitudinal ends,
wherein at least one of the electrically conductive sleeves forms a capacitor with a coil sleeve, wherein the coil sleeve is concentric with the at least one electrically conductive sleeve, and
wherein the coil sleeve is electrically insulated from the electrically conductive sleeve or the electrically conductive sleeves by a dielectric.

* * * * *